United States Patent [19]

Bezard et al.

[11] Patent Number: 4,874,242

[45] Date of Patent: Oct. 17, 1989

[54] DEVICE FOR DETECTION OF EXTRANEOUS SUBSTANCES THROUGH A WALL AND A SYSTEM FOR AIDING THE DRIVING OF AUTOMOBILES OR AIRPLANES

[75] Inventors: Jean-Jacques Bezard, Chaton; Philippe Feppon, Paris; Pierre Rodionoff, Courbevoie, all of France

[73] Assignee: Jaeger, Levallois Perret, France

[21] Appl. No.: 881,900

[22] Filed: Jul. 3, 1986

[30] Foreign Application Priority Data

Jul. 4, 1985 [FR] France ................................ 85 10277
Feb. 17, 1986 [FR] France ................................ 86 02093

[51] Int. Cl.$^4$ ...................... G01N 21/49; G60Q 1/08; G08B 21/00
[52] U.S. Cl. .................................. 356/341; 340/905; 340/602; 356/343
[58] Field of Search ............... 356/438, 439, 369, 364, 356/341, 342, 343; 340/62, 905, 601, 602,

[56] References Cited

U.S. PATENT DOCUMENTS

| | | | |
|---|---|---|---|
| 3,317,730 | 5/1967 | Hilsum ................................ 250/83.3 |
| 3,329,821 | 7/1967 | Lesage ................................ 250/565 |
| 3,521,232 | 10/1967 | Black ................................ 340/62 |
| 3,653,768 | 4/1972 | Menke ................................ 356/341 |
| 3,850,041 | 11/1974 | Seaman ................................ 73/495 |
| 4,092,068 | 5/1978 | Lucas et al. ................................ 356/73 |
| 4,155,651 | 5/1979 | Malone ................................ 356/341 X |
| 4,362,388 | 12/1982 | Egan et al. ................................ 356/341 |
| 4,365,896 | 12/1982 | Mihalow ................................ 356/446 |
| 4,371,864 | 2/1983 | Kawasaki et al. ................................ 340/62 |
| 4,575,249 | 3/1986 | Greiger ................................ 356/369 |
| 4,605,302 | 8/1986 | Löfgren et al. ................................ 356/5 |
| 4,608,551 | 8/1986 | Takeo et al. ................................ 340/62 |
| 4,647,207 | 3/1987 | Björk et al. ................................ 356/369 |
| 4,652,745 | 3/1987 | Zanardelli ................................ 250/227 |
| 4,665,351 | 5/1987 | Nyberg ................................ 340/602 X |

FOREIGN PATENT DOCUMENTS

| | | |
|---|---|---|
| 1573207 | 5/1970 | Fed. Rep. of Germany . |
| 2401906 | 9/1974 | Fed. Rep. of Germany . |
| 1168493 | 12/1958 | France . |
| 2214897 | 8/1974 | France . |
| 2187120 | 11/1974 | France . |
| 59-180441 | 3/1983 | Japan . |
| 544948 | 1/1974 | Switzerland . |
| 2034884 | 6/1980 | United Kingdom . |
| 1588289 | 4/1981 | United Kingdom . |
| 2060307 | 4/1981 | United Kingdom . |

Primary Examiner—Vincent P. McGraw
Attorney, Agent, or Firm—Fleit, Jacobson, Cohn, Price, Holman & Stern

[57] ABSTRACT

The invention relates to a device for detecting the presence of extraneous substances in a medium in the vicinity of a wall separating two mediums.

The device provides in the medium I illumination of a wall under a radiation corresponding to the transparency of the semi-transparency of the material of the wall on a reference illumination zone. Directional detectors permit covering of the reference illumination zone, the mean direction of the reception cone having with respect to the mean direction of the beam an inclination such that the intersection volume of the beam and of the reception cone is a minimum.

Application to the aid of driving of automobiles or airplanes and the control of industrial chemical processes is disclosed.

26 Claims, 9 Drawing Sheets

FIG_3

FIG_4

FIG_7a

FIG_7b

FIG_7c

DEVICE FOR DETECTION OF EXTRANEOUS SUBSTANCES THROUGH A WALL AND A SYSTEM FOR AIDING THE DRIVING OF AUTOMOBILES OR AIRPLANES

The present invention relates to a device for detection of the presence of extraneous substances in the vicinity of the surface of a separation wall between a first medium and a second medium.

Up till now the detection devices for extraneous substances such as deposits on walls or the like using optical systems are, essentially, restricted to detection as all or nothing of the transmissivity of the transparent wall to electromagnetic test radiation in the absence of a single deposited substance to be detected.

In the case where it is necessary to proceed to the detection of several substances, particularly a solid or liquid substance, or an intermediary physical state, liable to be deposited on the wall, and another substance such as a vapour, solid particles and/or aerosols in suspension in the second medium, the detection of the one or the other of the substances is not possible because of the masking effect or reciprocal saturation of corresponding detectors of one of the substances with respect to the other, particularly in the case of very different relative densities of the two substances.

In particular, there has been proposed in an article entitled "Mesure de la visibilite par capteur a microprocesseur (Measurement of the visibility by microprocessor detector)", published by S. Cain in the journal "Toute l'Electronique" no. 474 of May 1982, a device permitting detection of the presence of an aerosol or mist in free atmosphere.

Although this device effectively permits obtaining of the determination of a coefficient of absorption of electromagnetic radiation representative of the density of the aerosol or of the mist, this must be exclusively used either in free atmosphere or directly in a chamber in which the presence of the aerosol or of the mist is to be detected.

The use externally to this free atmosphere or this mentioned chamber, hence necessarily through walls limiting such an atmosphere or chamber cannot, in any case, be envisioned. The use of such a device in free atmosphere or in a chamber with a polluting or corrosive atmosphere cannot, either, be reasonably envisaged.

The present invention has the object of remedying the mentioned inconveniences by provision of a device for detecting the presence of extraneous substances in the vicinity of a separation wall between a first and a second medium, the substances and the device being separated by the wall.

Another object of the present invention is to provide a device permitting the detection in the same medium of a first substance liable to be deposited on one of the surface of a separation wall of this medium, called the second medium, of the other medium, called the first medium, in which the device is placed, and/or of a second substance such as a vapour, solid particles or aerosols in suspension in this second medium.

Another object of the present invention is to provide a system for aiding the driving of automobiles or airplanes using the mentioned detection device.

The device of detection of the presence of extraneous substances in the vicinity of the surface of a separation wall between a first and a second medium, the substances being positioned in the first and/or second medium, is remarkable in that is comprises, on the first medium side of the wall, means for illumination of the said wall, by means of a source of electromagnetic radiation of which the wavelength corresponds to the transparency or to the semitransparency of the constitutive material of the wall, these means permitting the illumination of the external surface of the wall by a beam of illumination in accordance with a reference illumination zone. First directional detector means sensitive to electromagnetic radiation, and of which the reception cone permits, in the region of the second medium surface of the wall, substantial covering of the reference illumination zone, are provided, the mean direction of the reception zone having with respect to the mean direction of the illumination beam, an inclination such that the volume resulting from the intersection of the illumination beam and of the reception cone to that of the second medium surface of the wall is a minimum.

The invention finds application in aiding the driving of automobiles or airplanes for the detection of the onset of icing, greasy or dusty deposits constituting dirtying of the windshield and possibly of second substances such as mist, smoke, or the like, the substances being situated outside the passenger compartment of the automobile and the device being situated inside the latter in the vicinity of the windshield. It finds particularly advantageous application for the surveillance of chemical or pharmaceutical processes, or in the manufacture of foodstuffs or other products in which the detection of substances in a receptacle having at least one transparent or semi-transparent wall on which the substances of the first type can be deposited or precipitated when the substances of the second type to be surveyed are able to appear in the receptacle or mentioned chamber.

The invention will be better understood from reading the following description and the study of the drawings in which:

FIGS. 6a, 6b, 6c show a detail of the preferred embodiment of the system such as shown in FIG. 5, FIGS. 7a, 7b, 7c show graphs or arrays of values permitting treatment of representative detective signals of the first and second type respectively, for a particular determined application or use.

FIGS. 8 to 12 are more especially relative to the ergonomics of a system of the invention, in the case where the latter is used for aiding the driving of an automobile.

The device for detecting the presence of extraneous substances in the vicinity of the surface of a separation wall between a first and a second medium will now be described in connection with FIG. 1.

In this figure, the separation wall between the first medium designated I and the second medium designated II is itself designated P. In an arbitrary, nonlimitative, manner the wall is shown by a parallel surface lamina P. In the present description, extraneous substances are considered to be positioned in the second medium II. Of course, the positioning of the extraneous substances in the medium I and/or the medium II is completely arbitrary, the detection device being for example arranged in the medium in which the extraneous substances are not present.

In accordance with the invention, the detection device comprises, on the first medium I side of the wall P, means, designated 1, for illumination of the wall P, by means of a source of electromagnetic radiation, of which the wavelength corresponds to the transparency or the semi-transparency of the constitutive material of the wall. By way of nonlimitative example, the wall P can be constituted by a glass wall and the electromagnetic radiation can be constituted by any radiation in the visible spectrum or in the near invisible spectrum, for example near infra-red.

Figure 1:
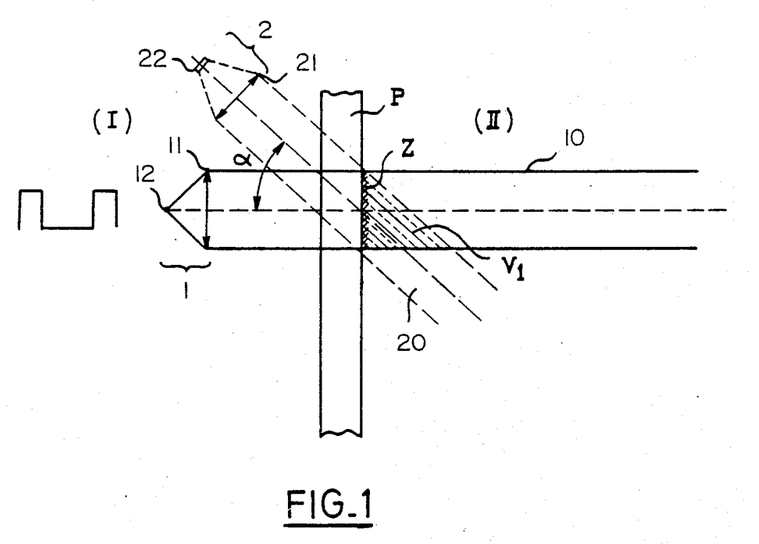
FIG. 1 shows a diagram of an embodiment of a device of the invention more specifically intended for the detection of solid liquid or pasty substances liable to be deposited or precipitated on the corresponding surface of the wall.

As appears further in FIG. 1, the illumination means 1 permit the illumination of the external surface of the wall P, that is to say the surface of the wall P on the second medium II side, by a beam of illumination designated 10 in a reference illumination zone, designated Z. Of course, the reference illumination zone designated Z is situated on the mentioned surface of the wall.

Further, first directional detector means designated 2, sensitive to electro-magnetic radiation and of which the reception cone designated 20 permits in the region of the second medium II face of the wall P substantial covering of the reference illumination zone Z are provided. As also appears clearly in FIG. 1, the mean direction of the reception cone 20 has, with respect to the mean direction of the illumination beam 10, an inclination designated $\alpha$ such that the volume $V_1$ resulting from the intersection of the illumination beam 10 and the reception cone 20 beyond the second medium II surface of the wall is a minimum.

Thus, for an intensity of illumination $I_i$, the first detector means 2 receive, as a function of the presence of one and/or the other substance of the first or second type, an energy $E_s$ according to the equation (I):

$$E_S = a_2 K(1-RS)^2 I_i + c_2 \cdot K \cdot RS(1-RS)I_i + d_2 \cdot K \cdot RS^2 I_i + b_2 \cdot RS \cdot I_i$$

In this equation, the expression $a_2 \times K \times (1-RS)^2 \times I_i$ represents the energy received by the first detector means taking account of losses in transmission across the wall and the first substance or substance of the first type deposited on the reference illumination zone Z, but without taking account of the energy thus diffused which will be able to be recovered. Similarly, the expression $b_2 \times RS \times I_i$ represents the diffusion energy coming from the wall and received by the first detector means, the substance of the first type deposited on the wall P being then comprised as an extended source of light. In the same manner, the expression $c_2 \times RS \times (1-RS) \times I_i$; $d_2 \times K \times RS^2 \times I_i$ shows the diffusion energy coming from losses in transmission across the substance of the first type deposited on the reference illumination zone Z, then retrodiffused by the substance of the second type and received by the detector. In the mentioned equation and the expressions explained above, the coefficients such as $a_2$, $b_2$, $c_2$ and $d_2$ are coefficients depending essentially on the geometry of the system.

In order to ensure an optimum detection of the substance of the first type deposited or precipitated on the wall and in particular on the medium II surface of this wall in the region of the reference illumination zone Z, it is advantageous, in the mentioned equation, to minimize the sum of the first two expressions explained above and on the contrary to maximize the third expression mentioned above. It is in particular advantageous, in accordance with the present invention, to provide an inclination of the mean direction of the illumination beam 10 with respect to the mean inclination of the reception cone 20 of the first detector means, such that the volume $V_1$, previously described, is a minimum in order to minimize the light energy retrodiffused by a substance of the second type possibly in suspension in the second medium designated II. It will thus be understood that the detection of the substance of the first type deposited on the wall particularly in the region of the reference illumination zone Z can thus be ensured independently of the presence or absence of one or any substance of the second type in suspension in the second medium designated II.

In order to obtain a good definition of the reference illumination zone Z, it is advantageous to utilise an illumination beam 10 of a substantially cylindrical crosssection. In the same manner, and in order to ensure a suitable recovering of the reference illumination zone Z by the reception cone 20 of the detector means 2, the mentioned reception cone 20 can advantageously be substantially convergent to the reception. By cone substantially convergent to the reception, is intended a cone converging in the direction of propagation of a given radiation, contained in the reception cone, towards the detector means 2.

As has already been described, the illumination beam 10 can be constituted by a composite beam of light in the region of the visible spectrum. It can equally advantageously be constituted by a substantially monochromatic illumination beam.

In order to ensure a sufficient rate of rejection of signals detected from parasitic radiation liable to be met in any industrial environment or other, it is advantageous, according to the present invention, to provide an illumination beam modulated in amplitude at a determined frequency of modulation. By way of non-limitative example, the frequency of modulation can be chosen, for an embodiment using conventional electronic components, up to values of 500 kHz. Preferably, and in order to obtain a particularly significant rate of rejection to parasitic frequencies of illumination of public lighting or the like, it is advantageous to choose a frequency of modulation not a multiple of 100 Hertz, any frequency being able, outside the mentioned values, a priori to be used.

As further appears in FIG. 1, the first detector means advantageously comprise, but in a non-limitative manner, a focussing lens 21, a diode or an assembly of photoreceptive diodes 22, sensitive to radiation from the illumination beam 10, and capable of generating an electric signal modulated to the frequency of modulation of the beam. The first detector means 2 further comprise a filter of central frequency centred on the value of frequency of modulation and delivering a filtered signal. Detection means are further able to generate a substantially continuous signal, representative of the amplitude of the filtered signal detected. A more detailed description of the electronic means utilised downstream of the detector means as such, described and shown in connection with FIG. 1, will be given later in the description.

As further appears in FIG. 1, the illumination means 1 comprise, for example, a photoemissive diode, designated 12, and a focussing lens designated 11, the photoemissive diode 12 and the focussing lens 11 being arranged in a manner to generate a substantially cylindrical illumination beam.

Further, as can be observed in FIG. 1, the optical axis of the focussing lens of the first detector means 2 and the optical axis of the focussing lens of the illumination means 1 are concurrent, substantially at the centre of the reference illumination zone Z, and forming an angle $\alpha$ less than 60°. The mentioned value of 60° depends particularly on the nature of the substances of the first type liable to be deposited on the corresponding wall P and of the nature of the second medium.

The focussing lenses 11 and 21, the photoemissive diode 12 and the photoreceptive diode 22 can be enclosed in tubes opaque to the wavelength of the illumination radiation, these tubes providing mounting. The mentioned tubes can have at one of their ends a sufficient opening for permitting the application of these latter onto the first medium I surface of the wall P opposite the reference illumination zone Z. A more detailed description of the mechanical arrangement of the device of the invention will be described later in the description.

The detection device, of the invention, as shown in FIG. 1, is remarkable in that it permits the detection of extraneous substances, such as solid, liquid or pasty substances deposited or precipitated on the second medium II surface of the wall P, particularly in the reference illumination zone Z, in the presence or in the absence of one or possibly several substances of the second type in suspension in the medium II. The minimum value of the volume $V_1$ of intersection between the illumination beam 10 and the reception cone 20 of the detector means 2 then permits avoidance of any phenomenon of saturation of the detector 2 by reason of the phenomenon of retrodiffusion of the radiation carried by the illuminating beam 10.

In particular, the device such as shown in FIG. 1, advantageously permits the detection of extraneous substances deposited on the windshield of an automobile or of an airplane, on the vitreous wall of a recipient permitting the carrying out of an industrial chemical process or the like.

A particularly advantageous embodiment of the invention will now be described in connection with FIG. 2.

In accordance with this Figure, the detection device of the invention comprises further, on the first medium I face of the wall P, second directional detector means, designated 3, sensitive to illumination radiation.

Thus, for the same intensity of emission $I_i$ or energy emitted, the equation (II) relating to the energy retrodiffused by the substance of the second type is given by:

$$E_b = a_1 K \cdot (1-RS)^2 \cdot I_i + c_1 \cdot K \cdot RS \cdot (1-RS) \cdot I_i + d_1 \cdot K \cdot RS^2 \cdot I_i$$

In this equation the coefficients $a_1, b_1, c_1$, represent coefficients relating to the geometry of the system.

In the mentioned equations (I) and (II), the coefficients K and RS represent respectively:

the coefficient of transmission of the light or energy of illumination from the substance of the second type in suspension in the medium II, the coefficient of loss through transmission of the substance of the first type deposited or precipitated on the wall P in the vicinity of the reference illumination zone Z. This coefficient is defined by the ratio of the incident energy, diminished by the transmitted energy, to the incident energy. It varies from zero, in the case of a wall proper, that is to say in the absence of deposit of substances of the first type to 1 in the case of total opacity.

The coefficient K of transmission of the light or illumination energy of the substance of the second type in suspension in the medium II is written in accordance with the equation (III):

$K = 4/V$ for a wavelength situated in the visible or near infra-red spectrum.

In this equation, v represents the visibility expressed in meters for a wavelength of the illumination considered.

For obtaining a maximum sensitivity of detection of the substance of the second type, it is then necessary to maximize the energy received by the mentioned detector means, as a function of the geometry of the system. To this end, the reception cone 30 of the second detector means 3, defines, in the region of the second medium surface, a reception zone R adjacent to the reference illumination zone Z. In an advantageous manner, the mean direction of the mentioned reception zone, has with respect to the mean direction of the illumination beam, an inclination such that the volume $V_2$ resulting from the intersection of the illumination beam 10 of the reception cone 30, beyond the second medium face of the wall P, is a maximum. Thus, the retrodiffusion energy from the substance of the second type for a given geometry, can be maximized and the sensitivity of detection is thus optimized.

By way of non-limitative example, the second detector means 3 can comprise a focussing lens 31 and a photoreceptive diode 32 or an assembly of diodes, sensitive to the radiation of the illumination beam 10, and able to generate an electric signal modulated to the frequency of modulation of the beam 10. In a manner analogous to the detection circuit connected downstream of the first detector means, the detection circuits connected downstream of the second detector means 3 can be comprised of a filter of central frequency fixed on the frequency of modulation of the illumination beam and detection means able to generate a continuous signal representative of the amplitude of the modulated signal detected.

A more detailed description of the circuits connected downstream of the second detector means 3 will be given later in the description.

Figure 3:
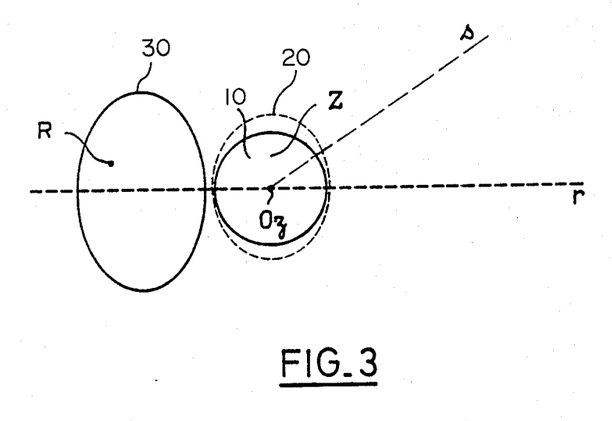
FIG. 3 shows an opposite view of the second medium separation wall surface, the surface on which the zone of illumination reception Z and the outline of reception cones of first and second detection means has been shown.

As further appears in FIG. 3, the optical axis of the focussing lens 31 of the second detector means 3 and the optical axis of the focussing lens of the illumination means 1 are concurrent and form an angle $\beta$ less than 15°. Of course, the inclination can be chosen as small as possible, in a manner to maximize the previously described volume $V_2$ and in consequence the quantity of retro-diffused energy able to be detected in the reception cone 30 by the second detector means 3.

In this Figure, the axis $O_z$, shown by a point, represents in fact the axis of the illumination beam 10, the axis $O_r$ represents the projection into the plane of the Figure of the axis of the reception cone 30 and the reception zone R previously described, and the axis $O_s$, shown also in broken lines, represents the projection into the plane of the Figure of the axis of the reception cone 20 previously described. Thus, it will be noted, in accordance with FIG. 3, but in a non-limitative manner, that the axes of the focussing lens of the illumination means and the axes of the first and second detection means are situated in two distinct cutting planes, as is shown in FIG. 3. Of course, these axes can possibly be arranged in a manner that the corresponding planes are formed in the same plane. The particular disposition as shown in FIG. 3, permits in particular ensuring a good compactness of the device. If necessary, a particular orientation, particularly of the illumination beam as a function of the important factors such as the illumination of a zone of the medium II determined particularly with a view to avoiding dazzling or in the case of an illumination with infra-red radiation, the inopportune illumination of fragile objects, such as for example individuals.

According to a particularly advantageous embodiment of the invention, the focussing lens 21 and 11 of the first detection means 2 and of the illumination means 1 have substantially the same aperture. Further, the focussing lens 31 of the second focussing means 3 can comprise an aperture greater in a ratio of 3 with respect to the aperture of the focussing lens 11 of the illumination means 1. These arrangements permit in particular ensuring at once a minimum volume $V_1$ and a maximum volume $V_2$, as has already been described.

Further, the point of intersection Ii of adjacent generatrices, in the first medium I of the illumination beam and of the reception cone of the second detector means 3 is situated in the second medium II in the vicinity of the second medium surface of the wall. By adjacent generatrix, is intended, it is emphasised, the generatrices of the illumination beam 10 and of the nearest of the generatrices of the reception cone 30, that is to say those which are shown in FIG. 2, in the medium I. Thus, advantageously, the point Ii can be situated at several centimeters from the medium II face of the wall P as is shown in FIG. 2. In this manner, the reception zone R is immediately adjacent the reference illumination zone Z and thus permits taking account of the appearance of the substance of the first type deposited on the reference illumination zone Z as well as on the reception zone R.

Figure 2:
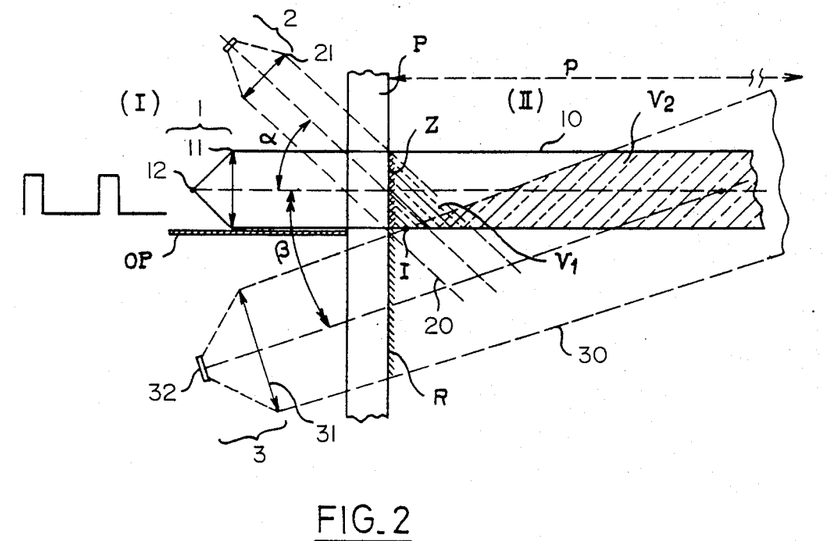
FIG. 2 shows a diagram of a preferred embodiment of the device of the invention, more particularly intended for the detection of one and/or the other of substances of a first type—solid, liquid, or pasty—liable to be deposited or precipitated on the corresponding surface of the wall and of a second type—vapour, solid particle or aerosol in suspension—in the second medium in the presence and/or the absence of the other substance and vice versa.

As a function of the desired application of the detection device of the invention, as shown in FIG. 2, it is advantageous to adjust the angle of inclination $\beta$ between the axis of the illumination beam 10 and the axis of the reception cone 30 so that the furthest point of intersection between the beam 10 and the cone 30 is situated at a distance p, called the span, representative of the use conditions of the detection device. In effect, this span is chosen so that the conditions of use of the geometry of the illumination beam and of the reception cones, the signal detected in the region of the second detector means 3 is sufficient for permitting a suitable representation of the density of the substance of the second type in suspension in the medium II. Thus, in the case of use for aiding the driving of automobiles or airplanes, it can be advantageous to adjust the distance p to several meters, whilst on the contrary in the case of use of the device for aiding the control of an industrial process, the distance p can be advantageously chosen to be several centimeters.

Figure 4:
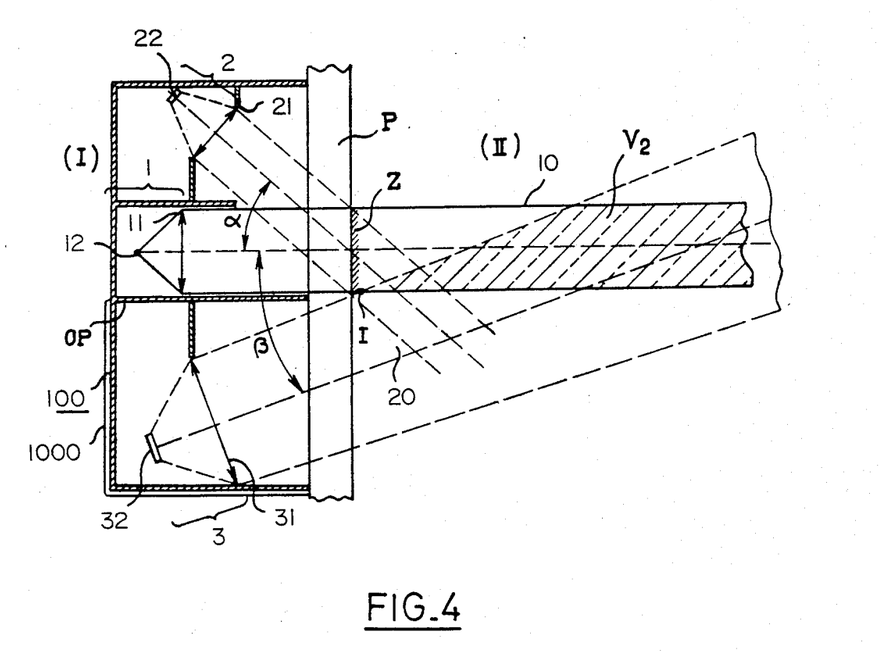
FIG. 4 shows, in cross-section on a longitudinal plane, a view of the complete device provided with its mechanical accessories.

Further, in order to ensure protection of the second detector means from the retrodiffused light energy from the substance of the first type deposited on the reference illumination zone Z as well as the light energy possibly reflected by the first medium surface of the wall P, the adjacent generatrices previously described situated in the first medium I of the illumination beam and of the reception cone 30 can advantageously be physically separated by an opaque wall, designated OP, at the wavelength of the illumination radiation. Of course and in a non-limitative manner, as is shown advantageously in FIG. 4, the wall OP can be arranged in the form of a tube designated 100, the tube enveloping further the second detector means and having in the region of these latter an electromagnetic screening 1000. It will be noted further that in FIG. 4, the tube can be arranged in the form of a box, in order to ensure the mechanical cohesion of the assembly consituted by the illumination means 1, the first detector means 2 and the second detector means 3. The electromagnetic screening 1000 shown in a partial manner in FIG. 4, can of course in an advantageous manner, be extended to the entire box, in order particularly to ensure a screening of the detection circuits, which will be described later in the description, to parasitic electromagnetic disturbances. This screening is also useful in a particular embodiment for emission at the wavelength of 930 nanometers with the emission power of 15 mW/steradian emitted on the axis of the illumination beam, the power of the retro-diffusion signal received, and thus received by the second detection means 3, varies between 100 and 2 nanoWatts. In these conditions, the detection region of the signal detected by the photodiode 32 does not exceed several microvolts. The preceding results have been obtained on detection of a substance of the second type such as water vapour, any substance such as an aerosol or solid particles such as smokes in suspenion in the second medium II, being also able to be detected. In this case, the first 2 and second 3 detector means have then been electronically coupled in a manner that the detected signal delivered by the first detector means 2 constitutes a correction reference signal vis-a-vis the detected signal delivered by the second detector means 3. The corrected signal is then representative of only the retrodiffusion of the illumination beam, by the second extraneous substance in suspension in the second medium II.

With a view to ensuring an optimization of the noise level of the detected signals and in particular reducing this as much as possible in order to obtain an optimum sensitivity of the system, it can be advantageous to provide that the emission of illumination radiation is effected in rectilinearly polarised light from a polariser. The reception in the region of the first and/or second detector means 2,3 is then effected by means of an analyser oriented in a manner to provoke attenuation of the light energy received by refelection on the wall P.

Further, and in an advantageous manner, the illumination beam 10 can be generated with respect to the wall P under incidence of Brewster, the polariser or the analysers then not being required.

A general description of a detection system according to the present invention will now be described with the help of the functional block diagram shown in FIG. 5.

The detection system presently described will be able to be used advantageously for aiding the driving of automobiles or airplanes particularly. In this particular case, the substances of the first type will be denominated dirt, that is to say substances such as dusts or greasy particles which will be deposted on the windshield of the automobile or of the airplane. In the case of an automobile, the device forming the fog receiver will also be positioned, in an advantageous manner, in one of the headlights of the vehicle, in the proximity of the glass wall of this.

In accordance with this mentioned diagram, the system has a dirt detector constituted by for example the first detector means 2 previously described as well as an emitter constituted by the illumination means 1 previously described. It can of course advatnageously also comprise a receiver 3 called the fog receiver constituted by the second detector means previously described. The assembly of mentioned elements is connected to a central unit 500 permitting the processing of signal sgiven by the previously described elements and their exploitation 700 for use.

Figure 5:
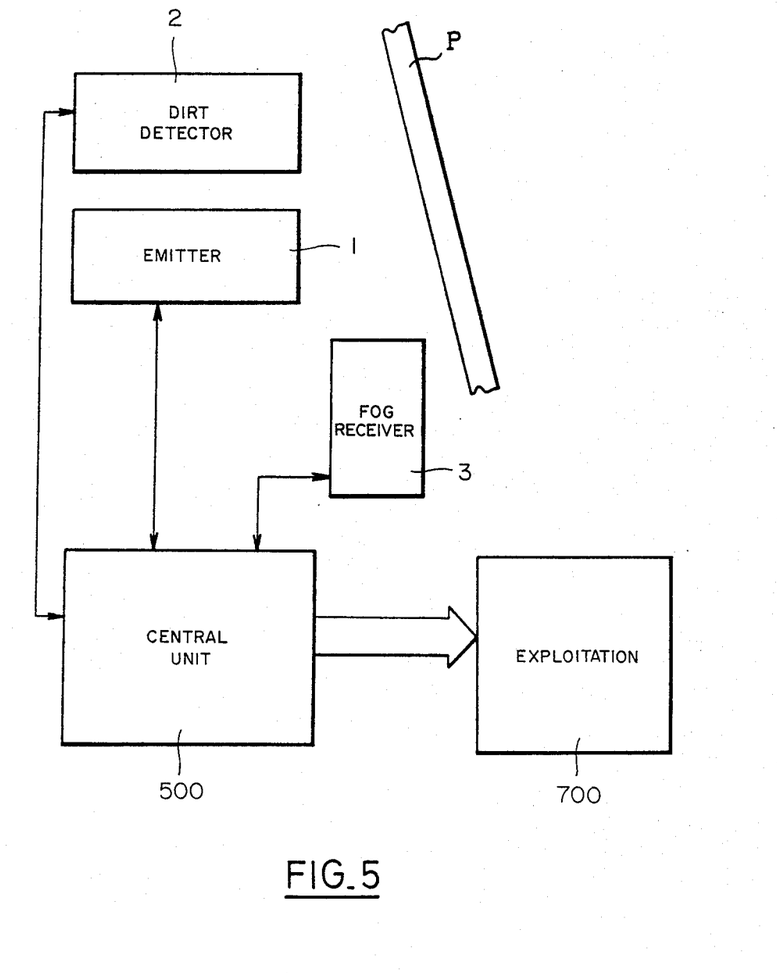
FIG. 5 shows a functional block diagram of a detection system of the invention, advantageously being able to be used for aiding the driving of automobiles or airplanes.

A detailed embodiment of the system such as shown in FIG. 5 will now be given in connection with the description of FIGS. 6a,6b and 6c and of FIGS. 7a,7b,7c.

Figure 6A:
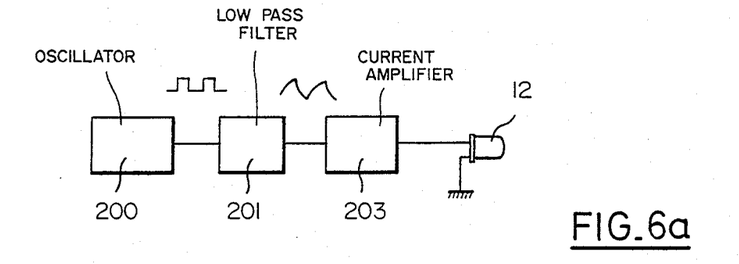
Figure 7A:
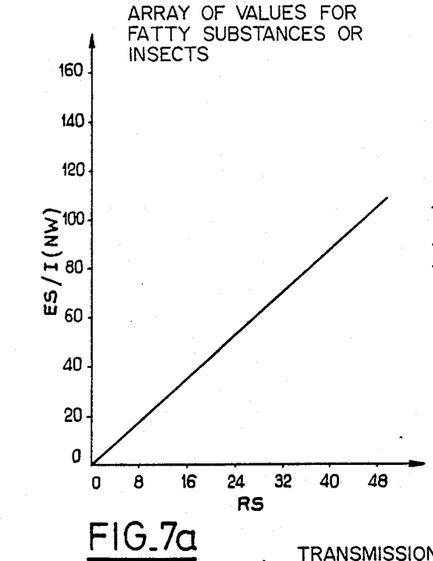
Figure 7B:
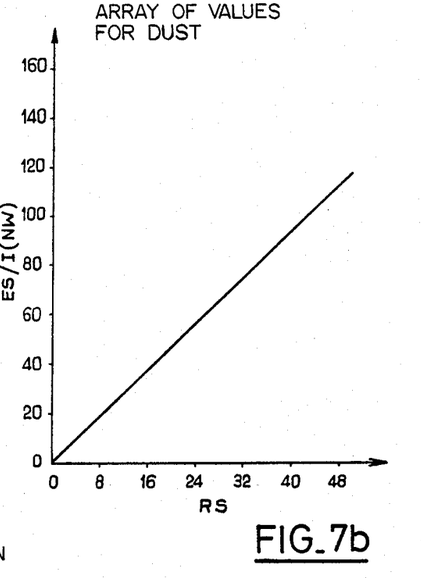
Figure 7C:
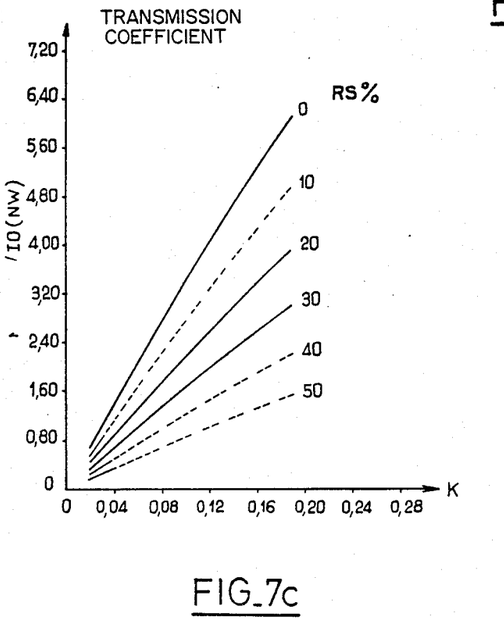

As shown in FIG. 6a, the illumination means comprise for example a modulation oscillator designated 200, delivering a rectangular modulation signal at a given frequency less than 500 kHz. The frequency can be chosen in a non-limitative manner at 2350 Herta. The oscillator 200 feeds a low-pass filter 201, which permits feeding a current amplifier 203 connected to one or several photoemissive diodes designated 12. The current amplifier 203 can be adjusted in a manner to deliver to the photo-emissive diode 12 a current of the order of 260 mA in order to ensure, at the wavelength of 930 nanometers, a mean emission power of the order of 15 mW/steradian.

Further, in an advantageous manner, the receivers such as described in FIG. 5 can be comprised from the reception photodiode designated 22 or 32, a detection circuit designated 303, amplifier means 302, a filter 301 centred on the modulation frequency of the illumination signals and finally, the modulation means designated 300, permitting the delivering of an alternating signal representative in amplitude of the intensity of the detected signals. By way of non-limitative example, the detection circuit 303 can advantageously be constituted by a circuit of parallel resonant type directly connected to the photoreceptive diode 22 or 32. The amplifier 302 can be constituted by a very high input impedance amplifier and a very low offset or shift current, the amplifier further constituting a low noise amplifier. It can advantageousl be constituted by an operational amplifier, comprising an input stage of the field effect transistor type with input impedance greater than 100 G ohms and offset or shift current of the order of 50 pA. In so far as the signals detected are detected in a noisy medium, and where it is necessary to amplify a signal from a very low level, as previously described, it is necessary that the filter 301 be a very selective and particularly stable filter. This can be constituted by commuted capacity filters with great stability and weak band passes of the order of 50 Hertz. The demodulation circuit 300 permits, from the filtered signal, the obtaining of a continuous signal, in a conventional manner, in order to delivery a continuous voltage proportional to the amplitude of the filter signal. In FIG. 6b are shown the signals designated B and S respectively proportional to the energy detected by the first detection means 2 and the second detection means 3. It will be understood that the signal B relates to the signal retrodiffused by the fog and the signal S relates to the signal retrodiffused by the dirt.

A more detailed description including of the central processing unit, such as shown in FIG. 5, will now be described in connection with FIG. 6c.

Figure 6B:
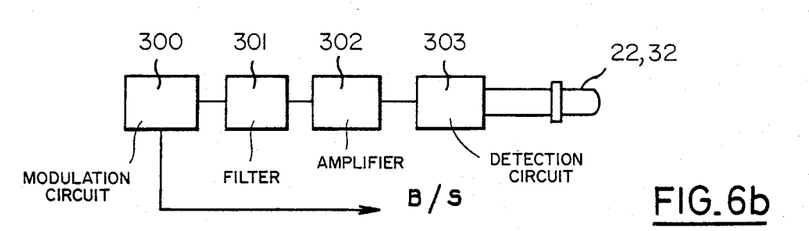
Figure 6C:
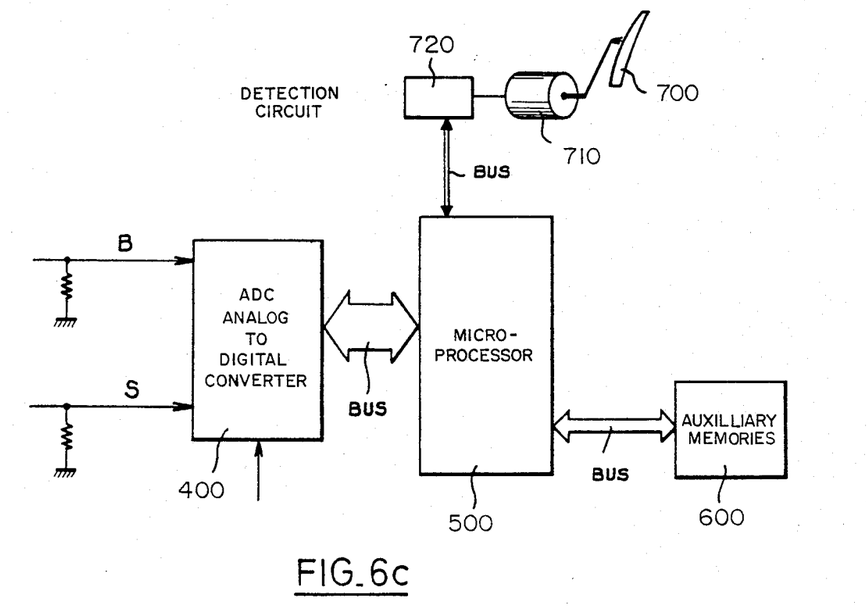

In this Figure, the signals B and S previously described in FIG. 6b, are received by an analog to digital converter means designated CAN and referenced 400, which are connected by a BUS type connection to a microprocessor designated 500. The microprocessor 500 may correspond to unit 500 shown in FIG. 5 and can be provided with peripheral circuits and particularly auxiliary memories, permitting the calculation of the coefficient of transmission of substances of the second type and in particular of fog, coefficient K, and of the coefficient of loss in transmission RS characteristics of dirt. These two coefficients are memorised in the auxiliary memories of the microprocessor 500 in an array of values or graphs such as shown in FIGS. 7a,7b, respectively relating to greasy bodies or insects and to dusts being able to be deposited or fixed on the windshield of the automobile or of the airplane and of transmission K for a substance of the second type such as water vapour for different value of coefficient of loss by transmission RS expressed in per cent. In FIGS. 7a,7b and 7c, the ordinates are graduated in nanowatts and the bscisses respectively for FIGS. 7a and 7b are graduated in the value of the coefficient of loss in transmission RS, whilst the abcisse for FIG. 7c is graduated in value of K. A program then permits from the measured values of RS in percent and the corresponding values of the signals B and S, to determine the value of the coefficient of transmission K and in accordance with the equation III, the value of the visibility v. According to the use required, as a function of the value of the visibility and/or as a function of the value of the coefficient of transmission K, a control can be made for ensuring different functions in the automobile or in the airplane. These functions can be for example, automatic control of the screen wash, on the appearance of a coefficient of loss in transmission RS of a high value, greater than 20 to 30% for example, control of the rear fog lamps as a function of the value of the coefficient of transmission K and modulation of the intensity of the light of these as a function of the value of the coefficient of transmission K and, in a suitable case, of the actual speed of the automobile. In FIG. 6c, has been shown the screen-wipers of the automobile or of the airplane as 700 conforming to exploitation 700 in FIG. 5. In accordance with an advantageous variant of the embodiment of the invention, the control morot of the screen-wiper 710 can be connected to a current detection circuit or of the feed voltage of the screen-wiper motor 710, this detection circuit being itself connected by the intermediary of a BUS connection for example, to the microprocessor 500. Thus, on operation of the screen-wiper of the automobile or of the airplane, the periodic wiping of the windshield by the balde of the screen-wiper in particular, has the effect of introducing periodically erroneous values of the measurement of the coefficient RS as well as in consequence of the coefficient of transmission K. In order to remedy the error thus introduced by the operation of the screen-wiper, it is advantageous from the current or feed voltage or the motor 710, to effect a synchronous correction, for example, to the values detected by the intermediary of the detection circuit 720. Further, it is also possible, in the absence of such a synchronous detection, to effect a lifting to the level of the memorised values in the auxiliary memories of the microprocessor 500, in order to detect periodically the maximum measured values. These maximum values can in the case where the periodicity corresponds to the periodicity of wiping by the screen-wiper, be suppressed or corrected in consequence from a program adapted for this.

Further, a supplementary function can consist in that the use circuit permits for example to display for the driver of the automobile a recommended speed as a function of the visibility. The practical embodiment of the mentioned functions from the values of the parameters or coefficient of transmission K and the loss in transmission RS, with respect to determined threshold values, uses devices or circuits of a known type and in consequence will not be described in detail.

Figure 8A:
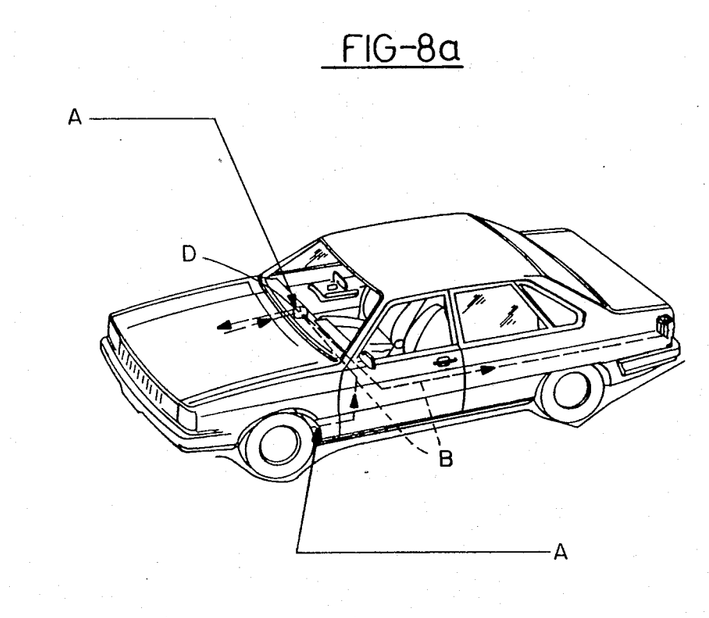
FIG. 8a shows an installation of a mist or fog detector, on board an automobile and FIG. 8b relates to the detection of fog with possibly an automatic control of rear fog lights with flashing if speed is very low or the automobile is stopped.
Figure 8B:
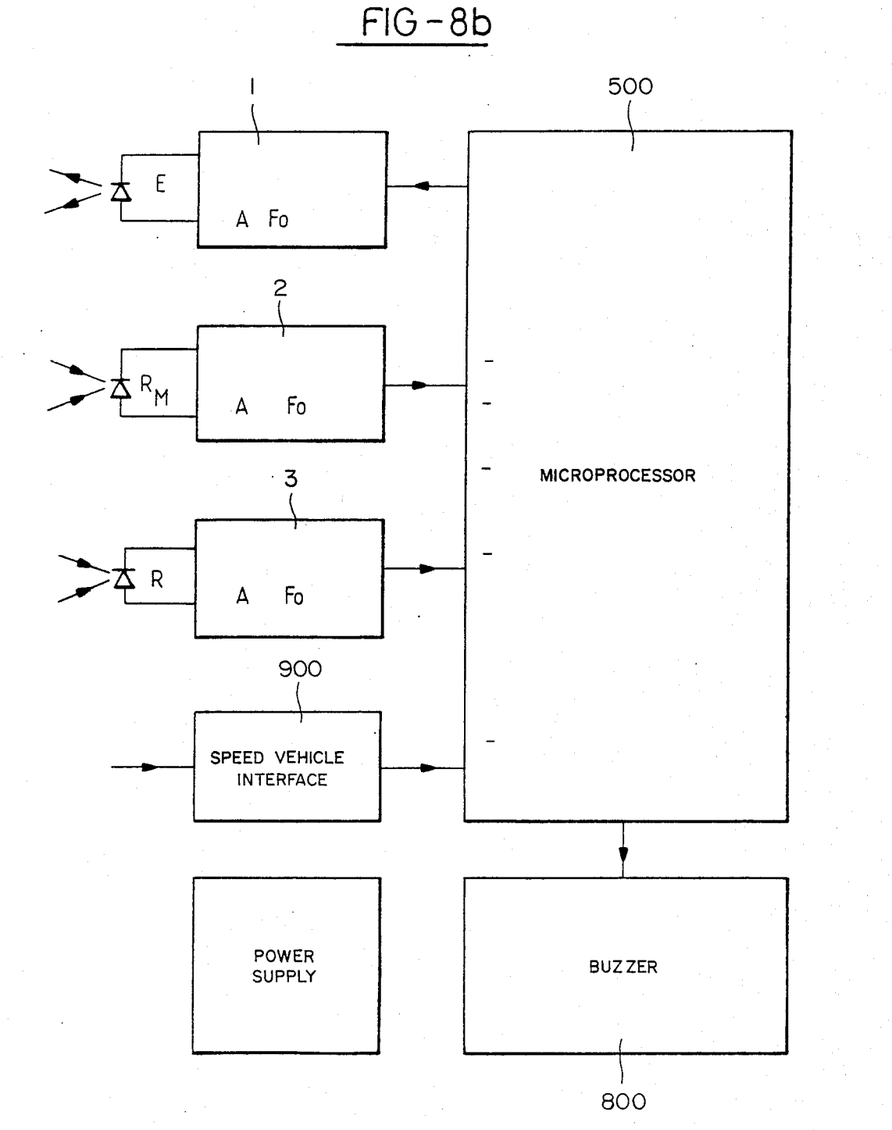
Figure 9A:
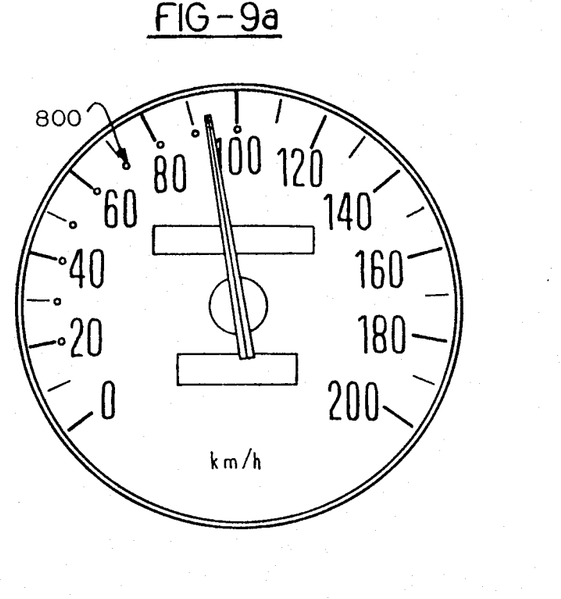
FIG. 9a shows a speedometer including recommended speed in fog and FIG. 9b shows a particular arrangement of the ergonomics of the system.
Figure 9B:
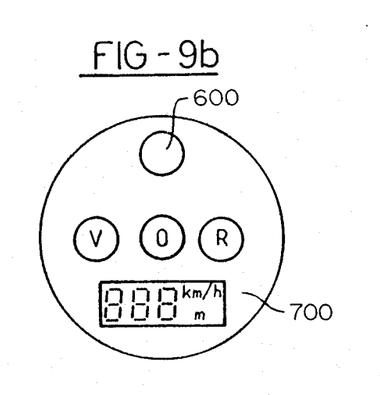
Figure 10:
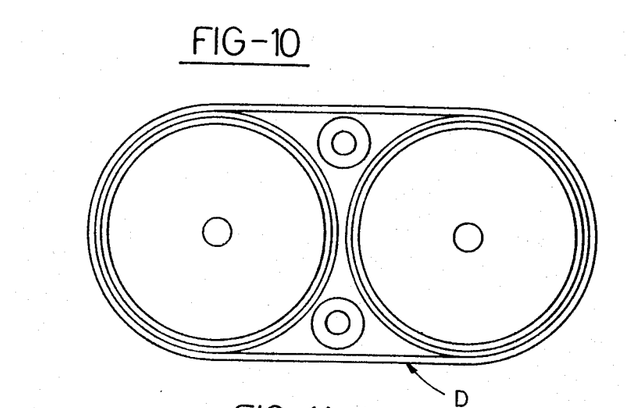
FIG. 10 shows a view of the detector device at the front of the automobile.
Figure 11:
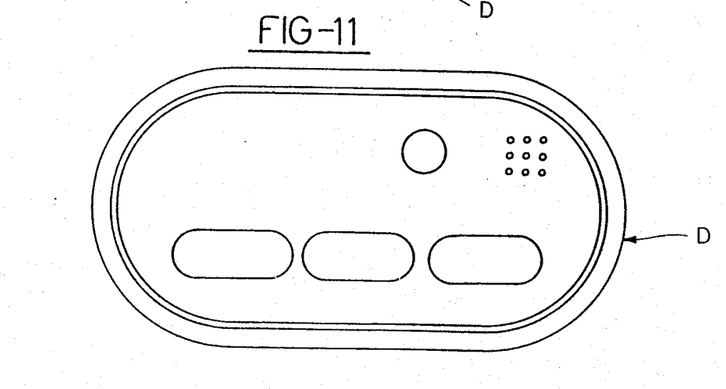
FIG. 11 shows a rear view of the detector device.
Figure 12:
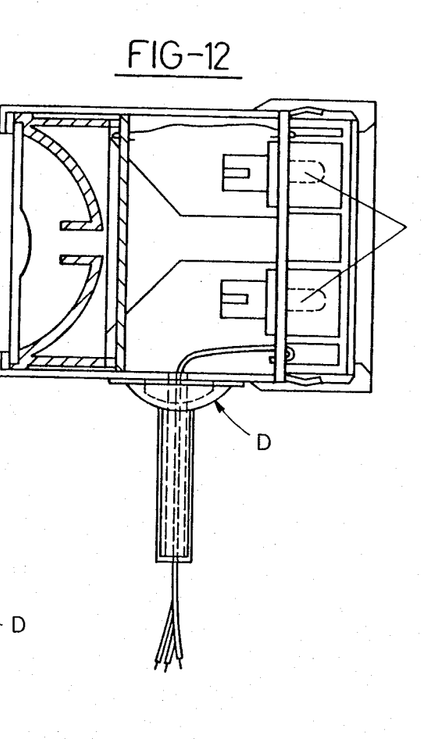
FIG. 12 shows a cross-section of FIG. 10 in the case of Cassegrain optics.

An ergonomic description of the system in the case where this is intended to aid the driving of an automobile will now be given in connection with FIGS. 8a to 12. In FIG. 8a, the arrows A and dotted lines B represent either normal connection lines of detectors, such as speed detector, or an IR beam.

From the visibility information and the speed information, it is possible to indicate to the driver, as a function of nominal chracteristics of the automobile, if he is driving too fast with respect to the visibility.

Dialogue by signal light and buzzer 800 Three signal lights are lighted in the following conditions:

| | |
|---|---|
| green | Speed $v<$ recommended speed |
| orange | Recommended speed $<$ speed $V<$ recommended speed $+$ 10 km/h |
| red | Speed $v>$ recommended speed $+$ 10 km/h |

With the red signal light the buzzer 800 is operated. In the absence of fog, no light is illuminated. A fourth service signal light indicates if the system needs to be cleaned.

An improvement of the preceding system consists in addition of indicating on an LCD display the recommended speed and the clear visibility distance.

Dialogue on the speedometer

This system consists in incorporating in the speedometer electroluminescent diodes of 10 by 10 km/h and to cause one of these to indicate the recommended speed, when there is fog. The comparison with the needle permits appreciation of the safety margin. The buzzer is operated for a speed $V>$ recommended speed $+10$ km/h. This device will also be able to be used at ends of recommended speed as a function of the flow of traffic for example, transmitted by beacon (cf. theme A: road information).

Control of rear fog lamp. One of the systems of dialogue with the drive previously described can be completed by a system of indication at the rear of the vehicle, allowing vehicles coming behind to be better warned. This system controls the rear fog lamps and makes them flash;

if the speed $V<$ recommended speed $-20$ km/h or on sudden thickening of the fog.

The light intensity for retinal traumatism for Lambda $<1.4$ micrometers is normally fixed at $0.1 \text{W/cm}^2$. We envisage an emitter of power $Pe<20$ mW, the surface of the emission pupil $>5 \text{ cm}^2$, that is 4 mW/cm² at zero distance, that is 1/25 of the permanent traumatism dose.

Example at 10 m opening of the beam spreading to 15 milliradians is 1 degree: diameter 150 mm cross-section of the beam 176 cm². That is P/S$=0.11$ mW/cm², that is 0.001 of the maximum dose.

In order to further limit the risk of permanent exposure, the system will be able to be stopped at low speed; and/or functioned at a reduced power in the case of close return, or again to use an optical emission more restricted $<s>50 \text{ cm}^2$ suppressing the risk.

Note: the power emitted by the device of the first embodiment ought not to exceed one milliwatt.

The base specification is, naturally, to detect the obstacle, but above all to provide to the driver acquisitions of recommended speed permitting him visual application of this in safety, so as to proceed manually at his slot.

This critical phase of "approach in safety" implies good awareness of the parameters of the obstacle and of the vehicle; actual speeds, relative distance, or, in a degraded manner, the "uncertain" couple distance-speed of approach, under reserve of which it does not return as a result of the safety of approach, particularly in the presence of multiple returns.

Taking account of specifications demanded, in the general manner of obstacle detectors, one can distinguish two main cases:

the obstacle is moving, at a distance and slow speed of approach. The term distance is preponderant over the term speed of approach, the obstacle is at a very slow speed as such and great distance. The important term is the high speed of approach, necessitating early detection.

One can immediately deduce the qualities necessary in the device:

at small distance, the Doppler information is quantitatively of little interest, and further difficult to arrange in the vicinity of zero beating. On the contrary, the telemetry msut be good;

at great distance, the precise telemetry is less important, compared with the qualitative information of "obstacle stopped".

The essential difficulty being then to not confuse the obstacle with the landscape (or worse in the landscape).

In summary the qualities are: good telemetry, optional Doppler information if the telemetry is derivable, good directivity, elmination of ground return. The two embodiments correspond to sophisticated technologies and high component and system costs.

The accompanying drawings illustrate schematically the invention and cause particularities to appear which form part of the invention. Thus FIGS. 8a and 10-12 show a detector device D which can be used at the front of an automobile in the above-described system.

There has thus been described a detection device permitting the detection of extraneous substances in a medium, one of the substances being able to be deposited on a separation wall of the medium, and the other substance remaining in suspension in the medium considered. This device appears particularly advantageous in that it permits very wide applications such as particularly aiding the driving of automobiles, in the absence of visibility, as well a the surveillance and control of industrial processes, particularly chemical industry processes, in which the passage of substances from vapour phase to solid phase must be detected.

We claim:

1. A device for detecting the presence of extraneous substances in the vicinity of the surface of a separation wall between a first and a second medium, the wall having a first medium surface exposed to the first medium and a second medium surface exposed to the second medium, the substances being positioned in said first or second medium, said device comprising, on a first medium side of said wall:

means for illumination of said wall by emans of a source of electromagnetic radiation having a wavelength which corresponds to the transparency or semi-transparency of the constitutive material of said wall, said means permitting illumination of the surfaces of said wall by an illumination beam in accordance with a reference illumination zone, first directional detector means sensitive to said electromagnetic radiation and having a first reception cone that permits, in the region of said second medium surface of said wall, substantial covering of said referenc eillumination zone, said reception cone having, with respect to said illumination beam, an inclination such that a volume resulting from intersection of said illumination beam and said reception cone beyond said second medium surface of said wall is a minimum, second directional detector means sensitive to said electromagnetic radiation, and having a second reception cone that permits in the region of said second medium surface the defining of a reception zone adjacent said refrence illumination zone, the second reception cone having, with respect to said illumination beam, an inclination such that a volume resulting from intersection of said illumination beam and said second reception cone beyond said second medium surface of said wall is a maximum, the illumination beam and the second rectpion cone having adjacent generatrices which intersect at a point of intersection situated in said second medium in the vicinity of said second medium surface of said wall, one of the extraneous substances being a solid, liquid or pasty substance deposited or precipitated on said second medium surface of said wall, particularly in said reference illumination zone, and a second extraneous substance detected being a vapor, aerosol, or solid particles in suspension in said second medium, said first and second detector means being electronically coupled in order that a first detected signal delivered by said first detector means constitutes a reference correction signal vis-a-vis a second detected signal delivered by said second detector means, said second detected signal being representative of retrodiffusion alone of said illumination beam by said second extraneous substance in suspension in said second medium.

2. A device according to claim 1, wherein said illumination beam is substantially cylindrical.

3. A device according to claim 1, wherein the first reception cone is substantially convergent.

4. A device according to claim 1, wherein said illumination beam is substantially monochromatic.

5. A device according to claim 1, wherein said illumination beam is modulated in amplitude at a determined modulation frequency.

6. A device according to claim 5, wherein said first detector means comprise:
a focussing lens,
a photoreceptive diode sensitive to the radiation from said illumination beam and able to generate an electric signal modulated at said frequency of modulation of said beam,
a filter with a central frequency centred on the value of said frequency of modulation, and delivering a filtered signal, and
detection means able to generate a substantially continuous signal representative of the amplitude of the filtered signal detected.

7. A device according to claim 6, wherein said illumination means comprise:
a photoemissive diode and
a foucssing lens, said photoemissive diode and said focussing lens being arranged in a manner to generate a substantially cylindrical illumination geam.

8. A device according to claim 6, wherein the optical axis of said focussing lens of said first detector means and the optical axis of said focussing lens of said illumination means are concurrent and form an angle less than 60°.

9. A device according to claim 6, wherein the said lenses, said photoemissive diode and said photoreceptive diode respectively are enclosed in tubes opaque to the wavelength of said illuminating radiation and for mign a mounting, said tubes having at one of their ends an opening sufficient for permitting the application of these latter on to the first medium surface of said wall opposite said reference illumination zone.

10. A device according to claim 1, wherein said reception cone of said second detector means is substantially convergent to the reception.

11. A device according to claim 1, wherein said second detector means comprise:
a focussing lens and
a photoreceptive diode sensitive to the radiation of said illumination beam and able to generate an electric signal modulated at a frequency of modulation of said beam,
a filter with central frequency centred on the value of frequency of modulation and delivering a filtered signal and
detection means capable of generating a substantially continuous signal representative of the amplitude of said filtered signal detected.

12. A device according to claim 11, wherein the optical axis of said focussing lens of said second detector means and the optical axis of a focussing lens of said illumination means are concurrent and form an angle less than 15°.

13. A device according to claim 11, wherein the optical axes of said focussing lenses of said illumination means and of said second detection means and of a focussing lens of said first detection means are situated in two distinct cutting planes or formed in the same plane.

14. A device according to claim 13, wherein said focussing lenses of said first detection means and of said illumination means have substantially the same aperture, and the focussing lens of said second focussing means has an aperture greater in a ratio of three with respect to said aperture of said focussing lens of said illumination means.

15. A device according to calim 1, including a wall opaque to the wavelength of the illumination radiation physically separating said adjcent generatrices in said first medium of said illumination means and of said reception cone of said second detector means.

16. A device according to calim 15, wherein said wall is in the form of a tube, said tube also enveloping said second detector means and having an electromagnetic screening property.

17. A device according to claim 1, including a polariser for effecting said emission of illuminating radiation as rectilinearly polarised light, and an analyser oriented to provoke an attenuation of the light energy received by reflection on said wall for effecting said reception in the region of one of said first and second detector means.

18. A device according to claim 17, wherein said illumination beam is generated with respect to the wall under incidence of Brewster the polariser or the analysers being then not required.

19. A system for aiding the driving of automobiles comprising a device according to claim 1, a microprocessor for control and processing of signals delivered by said detection device, said processing being effected in a manner to determine the coefficient of loss in transmission from a graph or array of values, and the coefficient of transmission from another graph or array of values.

20. A system according to claim 19, wherein the said microprocessor is connected to a use circuit permitting:
the functioning of a screen-wiper from a threshold value of the coefficient of loss by transmission,
the functioning of at least one fog lamp from a threshold value of said coefficient of transmission.

21. A system according to claim 20, wherein the light intensity of said anti-fog lamp is modulated as a function of the value of said coefficient of transmission and in the appropriate case the actual speed of said automobile.

22. A system according to claim 20, wherein said use circuit includes a display, for the driver of the automobile of a recommended speed as a function of the visibility.

23. A system according to claim 19, including:
a light signal of a first colour for indicating that the speed is lower than said recommended speed,
a light signal of a second colour for indicating that the speed is between said recommended speed and said recommended speed plus a predetermined amount,
a light signal of a third colour for indicating that the speed is greater than said recommended speed plus a predetermined amount,
a servic elight signal for indicating that said system requires to be cleaned, and
associated electronics for controlling said lights, from speed information and visibility information, as a function of nominal characteristics of said automobile.

24. A system according to claim 23, including a light display of said recommended speed and the distance of the visibility.

25. A system according to claim 23, wherein a speedometer comprises electroluminescent diodes, said recommended speed in the presence of fog being indicated by one of these diodes.

26. A system according to claim 22, including an audio signal of the buzzer type is operated for a speed greater than said recommended speed plus a predetermined amount.

* * * * *